(12) United States Patent
Nekrasov et al.

(10) Patent No.: US 7,427,508 B2
(45) Date of Patent: Sep. 23, 2008

(54) METHOD FOR ASSAYING MULTI-COMPONENT MIXTURES

(75) Inventors: Victor V. Nekrasov, Moscow (RU);
Rem Lazarenko-Manevich, Obinsk (RU); Jafar R. Gasanov, Moscow (RU);
Alexander T. Portyan, Moscow (RU);
Natalia V. Ryzhakova, Moscow (RU);
Yevgeny B. Brik, Obinsk (RU);
Vladimir R. Lazarenko-Manevich, Moscow (RU); Igor V. Fetisov, Moscow (RU); Oleg Lagutenko, Aventura, FL (US)

(73) Assignee: Organotek Defense System Corporation, Aventura, FL (US)

( * ) Notice: Subject to any disclaimer, the term of this patent is extended or adjusted under 35 U.S.C. 154(b) by 717 days.

(21) Appl. No.: 10/681,262

(22) Filed: Oct. 9, 2003

(65) Prior Publication Data

US 2005/0079628 A1 Apr. 14, 2005

(51) Int. Cl.
*G01N 24/00* (2006.01)
(52) U.S. Cl. .................................. 436/172; 436/164
(58) Field of Classification Search .................. None
See application file for complete search history.

(56) References Cited

U.S. PATENT DOCUMENTS 5,121,337 A * 6/1992 Brown .................. 702/28

OTHER PUBLICATIONS

Schmidt "A novel single beam optical spectrophotometer for fast luminescence-, absorption- and reflection-measurements of turbid materials", SPIE, Biochemical and MEdical Sensors, 1993, v. 2085, pp. 11-19.*

Voropai et al. "Determination of the luminscent impurity concentration in solution in the presence of intense background luminscence", J. Appl. Spectrosc., 2000, v. 67, No. 6, pp. 1030-1036.*

* cited by examiner

Primary Examiner—Yelena G Gakh
(74) Attorney, Agent, or Firm—Browdy and Neimark, P.L.L.C.

(57) ABSTRACT

A method and apparatus for identifying and differentiating multicomponent mixtures and identifying contamination thereof using direct comparison of characteristics of the analyte and characteristics of a standard sample of a known compound. These characteristics were obtained using methods and apparatus of spectrum analysis ensuring the possibility of receiving characteristic optical shapes (multi-dimensional signatures) of samples under comparison, which signatures represent a total set of spectral distributions of intensity values for light subjected to interaction with a sample, and the process of correlation of relative intensity values of light subjected to interaction with a sample at assigned wavelength. The comparison of different optical shapes (signatures) through comparing the respective intensity values at the assigned wavelength, ensures reliable identification of samples and obtaining information as to contamination or non-contamination, which may be identified afterwards by appropriate analytical methods.

6 Claims, 4 Drawing Sheets

METHOD FOR ASSAYING MULTI-COMPONENT MIXTURES

The present invention relates to analysis of substances and materials by optical methods, particularly for identifying and assaying multicomponent mixtures, as well as for analytical screening of trace amounts of contaminants in complex media, including potentially anthropogenic contaminants in objects of life support and the environment

BACKGROUND OF THE INVENTION

Practically all things, both natural and man-made, in any aggregative state, are multicomponent mixtures. Even superpure chemically individual substances that have been subjected to multiple purification steps always contain a set of trace impurities. For a number of reasons, it is nearly impossible, using current techniques, to separate these impurities from the desired component.

For example, even ideally purified deionized water contains trace amounts, at least, of dozens of humus impurities (Lavrik et al., 2000). Distilled spirits produced by the highest separation efficiency contain more than 200 trace components (Karagodin, 1998). Marketable cyclohexane contains up to 70 trace components (Dedkov, 2002). Yet these three entities are considered to be pure substances.

The situation with industrial products is much more complicated, because in making these products a certain set of impurity components are introduced as part of the process of production, and these impurities determine the quality and consumption features of a product. Other components, which are sometimes present in trace amounts, determine the safety of the product.

At present, about 80,000 kinds of chemical products are manufactured all over the world, most of which products are toxic to warm-blooded animals (Korte, 1996). The appearance of these substances in the environment and, particularly, in life support systems, poses a serious threat. The problem of water quality on the planet is particularly important, because 90% of the water is consumed for industrial use and is returned to the environment with wastewater (Dedkov, 2002). In fact, more than 500 individual man-made substances have been detected in wastewater, almost half of which are regarded as very dangerous, while the rest are characterized as dangerously harmful to vital functions and the functioning of ecosystems (Fortoutan-Red, 1982).

In other words, in practically all fields of human activities, there is a need for effective analytical techniques so that dangerous substances can be detected and eliminated.

Traditional methods for analyzing compounds in multi-component mixtures are usually based on selection of the analyte from the mixture, with further qualitative-quantitative correlation. This procedure requires a number of instrumental physical and chemical methods, often resulting in the requirement for preliminary treatment or concentration of a sample. Modern standardized analytical processes cover only about 20% of the total available set of components (Devjatykh et al., 1994). This results from the fact that the substances being analyzed may consist of tens and hundreds of individual compounds, and exhaustive analysis of the all of the components of a multicomponent mixture becomes a very long, laborious, and expensive procedure. At the same time, modern conditions dictate the requirement for rapid analysis methods which are simple in execution and which are able to rapidly detect the widest array of contaminants.

The methodology of analytical screening (Beyermann, 1982) relates to such methods, which itself is not strictly an analytical procedure. The essence of this methodology consists in rapid screening of suspicious objects requiring further standard by stricter methods. The parameters of these objects deviate from the parameters of standard object by any characteristic which is subject to rapid methods of instrumental control. It is evident that, for multicomponent mixtures, this characteristic is the identity or distinction of a compound in the product being analyzed, as compared with a standard compound which corresponds strictly with the manufacturer's process, or with a natural set of natural components wherein absence of the contaminants is confirmed. Thus, the solution of the task of rapid analysis does not require decoding of a qualitative-quantitative compound of a mixture. For that, it is quite enough to find an analytic method making it possible to receive some integral characteristic, or a set of characteristics, which can be measured instrumentally, ensuring unique identification of a compound in a mixture, and, at the same time, making it possible to detect qualitative changes of the compound at the level of trace amounts of a substance.

Optical spectrum methods of analysis are the most attractive for analyzing multicomponent mixtures. One peculiarity of optical spectra is the fact that they are characterized by complex reflection of both the component compound of the mixture and characteristics of individual components related to their chemical structure, and a complicated set of interactions of the components of the mixture with each other of a non-covalent nature (supra-molecular interactions [Lenn, 1995]. These interactions determine the per-molecular structure of a substance of nano-dimensional scale that is responsible for producing the optical spectra (Bakhshiev, 1972; Lakowicz, 1983; Suppan, 1990). In view of these circumstances, the optical spectra of multicomponent mixtures are uniquely sensitive to the slightest changes of a component in the mixture, which spectra appear both owing to mechanisms of intramolecular photonics and as a result of the influence of supramolecular interactions upon spectroscopic visualization of these mechanisms.

Photoabsorption methods are the most widely used analytical techniques. These methods are based on relative measurement of the light falling on a sample and passed through the sample. When these measurements are performed, systematic hardware inaccuracies are taken into account automatically, making these methods suitable for quantitative assessments. So, in particular, methods are known to analyze liquids for determining their identity or differences. Likewise, methods are known for determining contaminants in liquids, which methods consist of measuring absorption or reflectance spectra of an unknown liquid to determine characteristic spectra, finger prints, and/or profiles of data, and to determine the ratio of intensities of the light reflected or absorbed by a standard sample and a tested sample within the selected spectral section (Ingrum, 1991; Littlejohn, 1991). However, the absorption and reflectance spectra have low sensitivity and are ineffective for identifying trace amounts of impurities.

Figure 1:
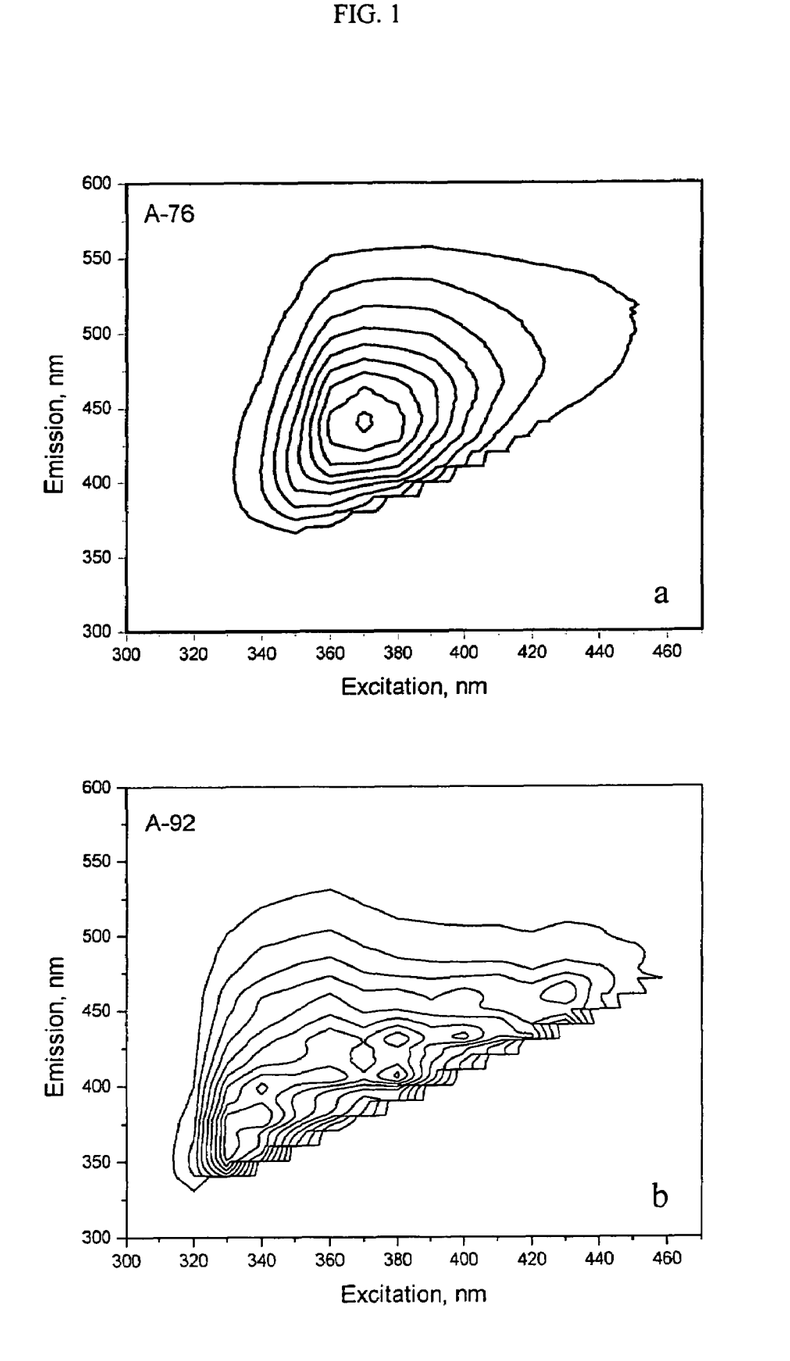
FIG. 1 shows contoured luminescence excitation-irradiation spectra of motor gasoline of different brands.

From Prior Art it is known that the luminescence spectra (Beyermann, 1982) are much more responsive to trace amounts of impurities and are very selective. At the same time, for identifying components of a mixture, three dimensional luminescence spectra (Webor, 1961) are most appropriate, which spectra reflect the complete set of spectral-luminescent characteristics of the test object. These spectra may be represented both as an isometric projection in coordinates of excitation wavelength and irradiation wavelength, or contoured spectra. Particularly, there is a known method for identifying a petroleum type by contoured luminescence excitation-irradiation spectra (Rho et al., 1978; Corfield et al., 1981). Also, very striking differences are observed for petroleum synthesis products. As an example for FIGS. 1 and 2 such data are given that were obtained by the present inventions. An illustration of this is found in FIG. 1 in which the contoured spectra for various brands of gasoline are shown.

Figure 2:
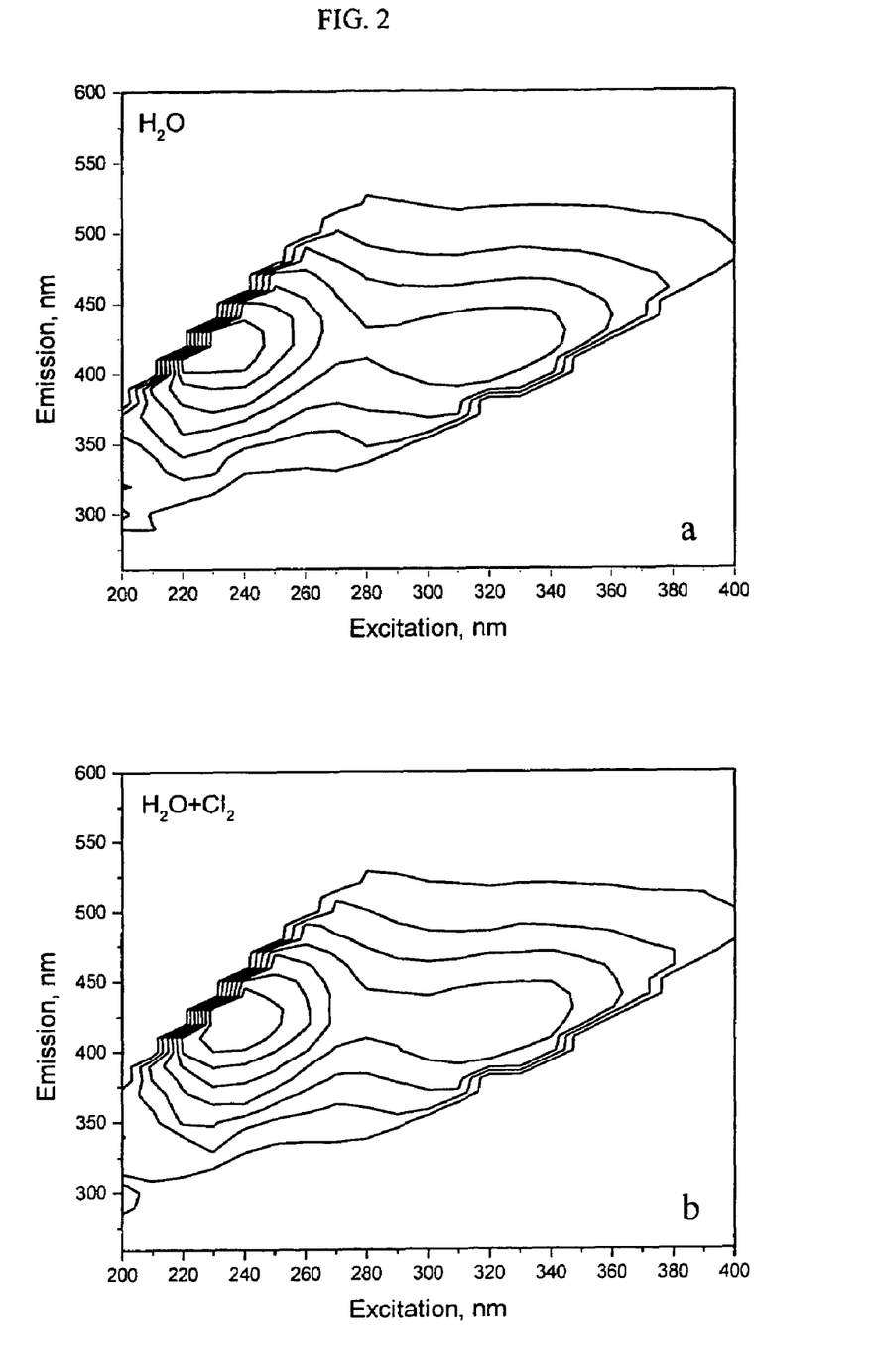

The drawbacks of the luminescence spectra are that the excitation-irradiation spectra are not able to display a complete component makeup of a sample, but only part of the components. To receive contoured spectra, mathematical interpolation software is used, which inevitably distorts the analysis result, making them of little use for correct identification and/or determination of differences for mixtures which are similar to each other. More, as stated in Siegel et al., 1985, visual analysis by three-dimensional spectra for mixtures containing more than three components presents a quite insoluble problem. For example, FIG. 2 shows the contoured spectra for luminescence of tap water and the same water with added chlorine. As one can see, the visual differences of contoured spectra for these samples are imperceptible.

The closest solution has been the method of identification of spirit-based liquids by the difference in matrices composed using a complex set of spectral profiles of a light transmission ratio, and luminescence profiles normalized for a unit, when excited by different wavelengths of light (Nekrasov, Russian Patent RU 2150699, 2000). This method totally excludes the human factor, resulting in positive identity and differences in trace amounts of impurities, even for objects which are very close in their composition (Nekrasov et al., Theses, 2000). The drawbacks of this method are that analytical matrices used for identification contain data of absolute measurements of the intensities being analyzed, and do not take into account the spectral light transfer ratio of the optical path of an analytic device, and the spectral responsiveness of photodetectors. This makes it impossible to correctly compare the analysis results and practically excludes their use in forming centralized electronic data banks. Also, during the actual measurement, noise caused by intensity fluctuations of the light source, being particularly perceptible in the ultraviolet range of the spectrum, is not taken into account, thus influencing the selectivity of the method and its possibilities for identification.

At the same time, the spectral characteristics used in the methods described above (Corfield et al., 1981; Siegel et al., 1985; Nekrasov, Russian Patent RU 2150699, 2000) reflect, mainly, only those components of a mixture that have pronounced chromophore characteristics and/or luminescence. In both absorption and luminescence of multicomponent systems, the components not having their own chromophore and luminophore characteristics are shown weakly. Both methods, by objective reasons have an analytical range which is restricted by the high concentrations of components of the mixture, resulting in drastic restriction of the possibilities of identification where there are high concentrations of characteristic components. These circumstances do not allow one, particularly for ultraclean substances and compounds, to use referencing of the objects into classes and to effectively use online features of communications networks and electronic data banks for identification. It makes it impossible to identify unknown objects in the physical absence of a standard sample of a compound.

SUMMARY OF THE INVENTION

It is an object of the present invention to overcome the aforesaid deficiencies in the prior art.

It is an object of the present invention to provide a method for determining the identity of multicomponent mixtures.

It is another object of the present invention to detect contaminants in multicomponent mixtures.

According to the present invention, a highly effective method is provided to determine the identity or differences between multicomponent mixtures, as well as to detect contaminants in multicomponent mixtures, by means of comparing the spectroscopic parameters set, which parameters completely characterize a complex of components in the mixture.

The present invention provides a reagentless express instrumental method for registering and analyzing electronic optical signatures that are formed during direct measurements of a complex set of photo absorption, luminescent and Raman spectral parameters of multicomponent mixtures. The complex set of absorption, luminescent and Raman spectral characteristics of an object is its unique identification characteristic. When comparing such set of measurable characteristics for an identifiable sample of an unknown mixture with an electronic digital image that has the same set of characteristics as the control sample of a known mixture, there is no need to identify each component of the mixture, (Nekrasov V. V, et al., pat RU 2150699, bull. No. 16, 2000). This method is suitable for forming dynamic computer-based data banks, making it possible to control the content of industrial products, life support systems, and the environment, as well as to prevent harmful and dangerous contaminations in these systems.

According to the present invention, the complex responsiveness of objects which are analyzed to the light influence by means of comparing absorption, luminescent, and Raman spectral characteristics of the object being analyzed. These characteristics were obtained while performing relative measurements of characteristics of compounds under analysis and characteristics of a standard sample and/or a calibration sample of a known compound by a quasi-doublebeam method ensuring calculation and compensation of systematic and random hardware inaccuracies directly during implementation of comparative measurements and/or with further mathematical treatment of the results.

A complex analysis using several complementary methods promotes increasing responsiveness and selectivity of the method (Beyermann, 1982). The high express degree of analysis is secured by obtaining the complete set of absorption, luminescent, and Raman spectral characteristics during the united analytical cycle of measuring and comparing the characteristics of samples under comparison in each of the selected points of the specific analytical range in one specialized analytical device, and/or while comparing the measured characteristics of a sample under analysis in an unknown mixture with the electronic signature of a standard sample of a known mixture.

Measurements of transmitted or reflected light are executed using standard methods, such as those shown in Weber, 1961 and Rabek, 1982. Intensity of luminescent light radiation radiated by a sample is measured in accordance with methods described by Lakowicz, 1983; Parker, 1968; and Rabek, 1982. At the same time, measurements are performed for intensity values of the exciting light $I_0$ at the excitation wavelength $\lambda_i$, and the intensity values of signals being measured are normalized for this value. Calculation and compensation of the light transfer ratio for an optical path of the registering and measuring apparatus are performed by means of the procedure of relative measurements of intensity values for the sample under analysis and a standard sample and/or specially prepared calibration sample of a luminescent mixtures with stable by time spectral and luminescent characteristics.

BRIEF DESCRIPTION OF THE DRAWINGS

FIG. 1 A shows the spectra for A-76. FIG. 1 B shows spectra for A-93.

FIG. 2 A shows contoured luminescence excitation-irradiation spectra of clean water. FIG. 2 B shows the same water containing an impurity of active chlorine.

LS—a light source, $\lambda_i$ SM—a device for selecting the narrowband probing irradiation, $F_1$—a device of focusing the probing ray;

SH—a holder of samples with a device for replacing a standard sample and a sample under analysis in the analytical channel: K is a standard sample of a known mixture, U is a sample under analysis of an unknown analyte;

$F_{2,3}$—devices for collecting the probing light $I_0$, the passed light $I_T$, and the luminescent light $I_L$ (or the Raman scattering $I_R$) to photodetector devices, $\lambda_j$ SM—a device for selecting the luminescence spectral components or the Raman scattering spectral components, $PD_1$, $PD_2$-photodetector devices for measuring the intensity values, accordingly, for the probing light and the passed light, and the luminescent light or the Raman scattering;

R&RM—a module of registration and treatment of signals including power and control units (remote control) of execution units, and a module of communication with an external computing device and/or a device for displaying the analysis results.

centralized municipal water supply system (curves 1-3);
the same water contaminated with municipal wastewater (curve 4);
the same water contaminated with 3,4-benzopyrene (curve 5);
the same water contaminated with petroleum derivatives (curve 6).

DETAILED DESCRIPTION OF THE INVENTION

The present invention can be described by the following non-limiting examples, which examples are given for illustration only and not for limitation.

Example 1 a. Light from a broadband source of optical radiation is divided into spectral components, and/or the assigned narrow spectral sections with a spectral width of $\Delta_i$ are selected from this light in the predetermined range of wavelengths $\lambda_i$ while ensuring the possibility of changing the spectral position of these sections with the assigned pitch $\Delta\lambda_i \geqq \Delta_i$. The selected narrowband probing light is then focused onto a sample under analysis.

b. A sample of a known mixture K and a sample of an unknown mixture U, are irradiated, by turns, with the focused probing beam at the assigned wavelength $\lambda_1, \lambda_2, \ldots \lambda_m$ from the predetermined spectral range $\lambda_i$;

c. Light falling on the sample, passed through the sample or reflected by the sample is collected at the photodetector, and the spectral components of the luminescent light is collected at another photodetector";

d. The intensity values of the probing light and the luminescent light on the photodetectors is measured for each of the selected wavelengths $\lambda_1, \lambda_2, \ldots \lambda_m$ of the predetermined spectral range $\lambda_i$. That is, the probing light $I_0$, the light passed through the sample or reflected by the sample $I_T$, and the luminescence light of the sample $I_L$, including steps of decomposition of the luminescent light into a variety of spectral sections, and/or sequential selection of the specified sections of wavelength $\lambda_1, \lambda_2, \ldots \lambda_n$ with a width $\Delta_j$, with the assigned pitch $\Delta\lambda_j \geqq \Delta_j$, where each section corresponds with the predetermined characteristic wavelength of the light in the predetermined spectral range $\lambda_j$, are collected onto the corresponding photodetectors and are measured;

e. The relative intensity of the collected light passed through the sample, or reflected by the sample, is determined at each of selected wavelengths $\lambda_m$, and the luminescent light for each of the selected wavelength $\lambda_m, \lambda_n$ for the known mixture and unknown mixture, in accordance with the following expressions:

$$T^K(\lambda_m) = \frac{I_T^K(\lambda_m)}{I_0^K(\lambda_m)}; \quad T^U(\lambda_m) = \frac{I_T^U(\lambda_m)}{I_0^U(\lambda_m)};$$

$$L^K(\lambda_m, \lambda_n) = \frac{I_L^K(\lambda_m, \lambda_n)}{I_0^K(\lambda_m)}; \quad L^U(\lambda_m, \lambda_n) = \frac{I_L^U(\lambda_m, \lambda_n)}{I_0^U(\lambda_m)},$$

where $T^K(\lambda_m), T^U(\lambda_m)$—intensity values of passed or reflected light for samples of the known K mixture and unknown U mixture, normalized for the intensity of incident radiation falling on the sample at the corresponding wavelength;

$L^K(\lambda_m, \lambda_n), L^U(\lambda_m, \lambda_n)$—intensity values of the luminescent light irradiated by the sample of the known K mixture and unknown U mixture within the specified sections $\lambda_1, \lambda_2, \ldots \lambda_n$ of the predetermined range of wavelengths $\lambda_j$ with light excitation within the specified sections $\lambda_1, \lambda_2, \ldots \lambda_m$ of the predetermined range of wavelengths $\lambda_i$, normalized for intensity of incident radiation falling on the sample at the corresponding wavelength;

$I_T^K(\lambda_m), I_T^U(\lambda_m)$—intensities of passed or reflected light for samples of a known K mixture and an unknown U mixture measured at the specified sections $\lambda_1, \lambda_2, \ldots \lambda_m$ of the predetermined range of the incident light from the predetermined range $\lambda_i$;

$I_L^K(\lambda_m, \lambda_n), I_L^U(\lambda_m, \lambda_n)$—intensities of the luminescence radiated by a sample of a known K mixture and a sample of an unknown U mixture measured at the selected wavelength $\lambda_1, \lambda_2, \ldots \lambda_n$ of the extracted range of wavelengths $\lambda_j$ with light excitation within the specified sections $\lambda_1, \lambda_2, \ldots \lambda_m$ of the predetermined range of wavelengths $\lambda_i$;

$I_0^K(\lambda_m), I_0^U(\lambda_m)$—intensity of incident probing radiation falling on the appropriate samples at the time of performing measurements;

f. The corresponding relative intensity values of the light passing passed through a the sample, or reflected by a the sample, on each of extracted selected wave-length wavelength $\lambda_m$, and the luminescent light for each of the extracted selected wave-length wavelength $\lambda_m, \lambda_n$ for a known mixture and an unknown mixture are compared, and the compliance between the unknown mixture and the known mixture is defined determined by the following expression:

$$A = \frac{1}{2} \times \left( \frac{1}{m} \times \sum_{m=1}^{m} \frac{T^U(\lambda_m)}{T^K(\lambda_m)} + \frac{1}{m \times n} \times \sum_{m=1}^{m} \sum_{n=1}^{n} \frac{L^U(\lambda_m, \lambda_n)}{L^K(\lambda_m, \lambda_n)} \right) = 1 \pm \delta,$$

where m, n—the number of selected wavelengths from the predetermined spectral ranges $\lambda_i$ and $\lambda_j$, respectively;

$\delta$—a value of allowable deflections of the compared values for the unknown mixture under analysis from the corresponding values for the similar values of a standard sample of a known mixture;

g. The presence or absence of foreign impurities contaminants) in the mixture under study is determined by the following expressions:

$$C_T(\lambda_i) = \frac{T^U(\lambda_{m+1})}{T^K(\lambda_{m+1})} - \frac{T^U(\lambda_m)}{T^K(\lambda_m)};$$

$$C_L(\lambda_i, \lambda_j) = \frac{L^U(\lambda_{m+1}, \lambda_{n+1})}{L^K(\lambda_{m+1}, \lambda_{n+1})} - \frac{L^U(\lambda_m, \lambda_n)}{L^K(\lambda_m, \lambda_n)};$$

whereas, if $C_T(\lambda_i) = C_L(\lambda_i, \lambda_j) = 0 \pm \delta$, the foreign impurities in the sample under analysis are absent, while if there are ranges with $C_T(\lambda_i) > 0 \pm \delta$, and/or $C_L(\lambda_i, \lambda_j) \neq 0 \pm \delta$ the conclusion can be drawn that the undesirable impurities are present.

Example 2

In another embodiment of the present invention, the procedure differs from the procedure of Example 1 as follows: the step of comparing the unknown sample with the known one is replaced with the step of comparing their electronic absorption-luminescent signatures (ALS), for which purpose the following steps are to be added:

a. A calibration sample Q is prepared, which calibration sample represents a specially made-up mixture or a multi-component solution, the absorption or reflectance spectra, and luminescence spectra of which solution (mixture) are overlapped with the corresponding spectra of the known mixture within the predetermined analytical spectral ranges $\lambda_i$ and $\lambda_j$, i.e. have nonzero intensity in the specified ranges;

b. The standard sample of a known K mixture and the calibration Q sample are placed into an analytical device;

c. Measurements and transformations of measured values for intensity of the light passed through or reflected by standard and calibration samples, and their luminescent light, are performed in accordance with steps a-e of Example 1, while taking into account the step of replacing the unknown U sample with the calibration Q sample;

d. An electronic absorption-luminescent signature $ALS_K$ of a standard sample is created as follows:

$$ALS_K = \|K_E\| = \left\| \begin{pmatrix} \left(\frac{T_1^K}{T_1^Q}\right) & \left(\frac{L_{1,1}^K}{L_{1,1}^Q}\right) & \cdots & \left(\frac{L_{1,n}^K}{L_{1,n}^Q}\right) \\ \cdots & \cdots & \cdots & \cdots \\ \left(\frac{T_m^K}{T_m^Q}\right) & \left(\frac{L_{m,1}^K}{L_{m,1}^Q}\right) & \cdots & \left(\frac{L_{m,n}^K}{L_{m,n}^Q}\right) \end{pmatrix} \right\|,$$

where:

$T_m^K$ intensities of the passed or reflected light $I_T$ of a sample of a known K mixture, normalized for intensities of the probing light $I_O$, measured at the frequencies $\lambda_m$;

$L_{m,n}^K, L_{m,n}^Q$—intensities of the luminescence radiated by a sample of a known K mixture and a calibration Q sample, normalized for intensities of the probing light $I_O$, measured at the frequencies $\lambda_n$ with the excitation at the frequencies $\lambda_m$;

e. An electronic signature of a standard sample $ALS_K$ is entered into the computer database, and/or is saved on an intermediate medium;

f. Steps similar to those in step c of this embodiment are carried out with the sample of an unknown mixture, including the step of replacing the standard sample K with the calibration sample Q, which is strictly identical with the calibration sample used when measuring a standard sample, and creating an electronic signature $ALS_U$ of a sample under analysis:

$$ALS_U = \|U_E\| = \left\| \begin{pmatrix} \left(\frac{T_1^U}{T_1^Q}\right) & \left(\frac{L_{1,1}^U}{L_{1,1}^Q}\right) & \cdots & \left(\frac{L_{1,n}^U}{L_{1,n}^Q}\right) \\ \cdots & \cdots & \cdots & \cdots \\ \left(\frac{T_m^U}{T_m^Q}\right) & \left(\frac{L_{m,1}^U}{L_{m,1}^Q}\right) & \cdots & \left(\frac{L_{m,n}^U}{L_{m,n}^Q}\right) \end{pmatrix} \right\|,$$

where $T_m^U$—intensities of the passed or reflected light $I_T$ of a sample of an unknown U mixture, normalized for intensities of the probing light $I_O$, measured at the frequencies $\lambda_m$;

$L_{m,n}^U$—intensities of the luminescence radiated by a sample of an unknown U mixture, normalized for intensities of the probing light $I_O$, measured at the frequencies $\lambda_n$ with the excitation at the frequencies $\lambda_m$;

g. Comparing electronic signatures of the unknown mixture $ALS_U = \|U_E\|$ being tested with similar data for the standard sample of the known mixture $ALS_K = \|K_E\|$ by the following expression:

$$\|A_{ALS}\| = \frac{\|U_E\|}{\|K_E\|},$$

so that a conclusion on the identity of the unknown mixture and the certain mixture may be drawn when all elements of the matrix $\|A_{ALS}\|$ contain only unit elements (i.e. $a_i = a_{i,j} = 1 \pm \delta$);

h. To determine the presence or absence of unwanted contaminants for the mixture under study by the following expression:

$$\|C_{ALS}\| = \frac{\|U_E\| - \|K_E\|}{\|K_E\|},$$

wherein, if the matrix $\|C_{ALS}\|$ comprises nonzero elements, the values of which exceed the value of allowable deflection from the corresponding values of the standard sample of the known mixture, $|c_i, c_{i,j}| > |\pm\delta|$, the sample under analysis is defined as containing the unwanted contaminants;

Example 3

This example differs from Example 1 as follows: a step is added to measure intensity values of Raman scattering of he sample under analysis and the standard sample, for which purpose the following steps are to be added:

a. The samples of the unknown mixture and the known mixture are irradiated, by turns, with a monochromatic line of a narrowband (lined) source of light at one or several selected fixed frequencies $v_{ex}$;

b. The exciting light $v_{ex}$ is collected onto the photodetector, and spectral components of the Raman scattering light $I_R$ are selected and collected onto another photodetector;

c. For each of the selected frequencies $v_1, v_2, \ldots v_p$ of the predetermined spectral range, intensity values of the exciting light and light of the Raman scattering collected onto the photodetectors are measured, namely: the exciting light falling on a sample $I_{ex}$, and the light of Raman scattering of a sample $I_R$, including steps of decomposition of the light of Raman scattering into a variety of spectral sections, and/or sequential selection of the specified frequency sections $v_1, v_2, \ldots v_p$ with a width of $\Delta_r$, with assigned pitch $\Delta v_r \geqq \Delta_r$, where each section corresponds to the predetermined characteristic frequency of the light in the predetermined spectral range $v_r$, are collected onto the corresponding photodetectors and are measured;

d. The relative intensity of the collected light of Raman scattering at each of the selected wavelengths frequencies $v_1, v_2, \ldots, v_p$ for a known and unknown mixtures is determined in accordance with the following expressions:

$$R^K(v_{ex}, v_p) = \frac{I_R^K(v_{ex}, v_p)}{I_{ex}^K}; \quad R^U(v_{ex}, v_p) = \frac{I_R^U(v_{ex}, v_p)}{I_{ex}^U};$$

where:

$I_R^K(v_{ex}, v_p), (I_R^U(v_{ex}, v_p)$—intensity of Raman scattering radiated by a sample of a known K mixture and a sample of an unknown U mixture within the specified sections $v_1, v_2, \ldots v_p$ of the predetermined frequency range $v_r$ with light excitation at one of the selected frequencies $v_{ex}$;

$I_{ex}^K, I_{ex}^U$—intensity of the exciting light falling on corresponding samples at the time of performing measurements;

f. Data for the unknown mixture being tested with are compared with similar data for the standard sample of the known mixture by the following expression:

$$A = \frac{1}{2} \times \left(\frac{R^U(v_{ex}, v_p)}{R^K(v_{ex}, v_p)}\right) \times$$

$$\left(\frac{1}{m} \times \sum_{m=1}^{m} \frac{T^U(\lambda_m)}{T^K(\lambda_m)} + \frac{1}{m \times n} \times \sum_{m=1}^{m} \sum_{n=1}^{n} \frac{L^U(\lambda_m, \lambda_n)}{L^K(\lambda_m, \lambda_n)}\right)$$

wherein the known mixture and unknown mixture are determined as being identical if $A = 1 \pm \delta$;

Example 4

This method differs from that of Example 2 as follows: comparison is performed for electronic signatures containing spectral profiles of absorption, luminescence and Raman scattering intensities for the unknown mixture sample ($RALS_U$) and the standard sample ($RALS_K$), which are formed by the method of Example 3, resulting in the following step of normalization of Raman matrixes in the following way:

a. A calibration sample $Q_R$ is prepared, which calibration sample represents a specially made-up mixture or a multi-component solution, the luminescence spectrum of which overlaps with the Raman spectrum of the known mixture within the predetermined analytical spectral ranges;

b. The intensity of Raman scattering is measured, and the results are converted similarly to steps b-f of Example 2. The signatures of the standard sample and the sample are formed in accordance with the following expressions:

$$\|K_R\| = \left\| \begin{pmatrix} \frac{R_{1,1}^K}{L_{1,1}^{Q_R}} \end{pmatrix} \cdots \begin{pmatrix} \frac{R_{1,p}^K}{L_{1,p}^K} \end{pmatrix} \\ \cdots \cdots \cdots \\ \begin{pmatrix} \frac{R_{q,1}^K}{L_{q,1}^{Q_R}} \end{pmatrix} \cdots \begin{pmatrix} \frac{R_{q,p}^K}{L_{q,p}^{Q_R}} \end{pmatrix} \right\|, \| U_R \| = \left\| \begin{pmatrix} \frac{R_{1,1}^U}{L_{1,1}^{Q_R}} \end{pmatrix} \cdots \begin{pmatrix} \frac{R_{1,p}^U}{L_{1,p}^K} \end{pmatrix} \\ \cdots \cdots \cdots \\ \begin{pmatrix} \frac{R_{q,1}^U}{L_{q,1}^{Q_R}} \end{pmatrix} \cdots \begin{pmatrix} \frac{R_{q,p}^U}{L_{q,p}^{Q_R}} \end{pmatrix} \right\|,$$

where $R_{q,p}^K, R_{q,p}^U$—intensity values of Raman light scattering, normalized for intensity of the exciting light $I_{ex}$, for samples of the known K mixture and the unknown U mixture, measured at the frequencies $v_p$ with light excitation at the frequency $v_q$;

$L_{q,p}^{Qk}$—the luminescence intensity for a calibration sample $Q_R$, normalized for the intensity of the exciting light $I_{ex}$;

c. The electronic signatures of an unknown mixture $\|U_E\|$ being tested are compared with similar data for a standard sample of the known mixture $vK_E\|$, including the step of comparing Raman matrixes ($RALS_{U,K}$), by the following expression:

$$\|A_{RALS}\| = \left(\frac{\|U_R\|}{\|K_R\|}\right) \times \left(\frac{\|U_E\|}{\|K_E\|}\right),$$

where the identity of samples is determined by the following attribute: $\|A_{RALS}\| = 1 \pm \delta$;

Example 5

The process of this embodiment differs from the processes of Examples 1 and 2 as follows: a step is added to dissolve samples of the mixture under analysis and the certain standard mixture in appropriate for these mixtures solvents.

The most effective realization of the complex analysis system of the present invention is performed by a specialized multifunctional measuring device which is able to perform relative measurements of absorption spectra and luminescence, as well as Raman scattering, for samples under comparison in a common analytic cycle. This makes it possible to minimize both systematic and random inaccuracies of measurements, and provides a high degree of reliability.

The apparatus of the present invention is illustrated in block diagram in FIG. 3a. This diagram includes all of the functions of the analytical steps required for the analysis of the present invention.

To perform complex measurements of absorption spectra, luminescence and Raman scattering, a combined light source is used consisting of continuous and line light sources LS, and a matching device, thereby ensuring the possibility of switching and focusing the light from the required source onto a sample.

Figure 3:
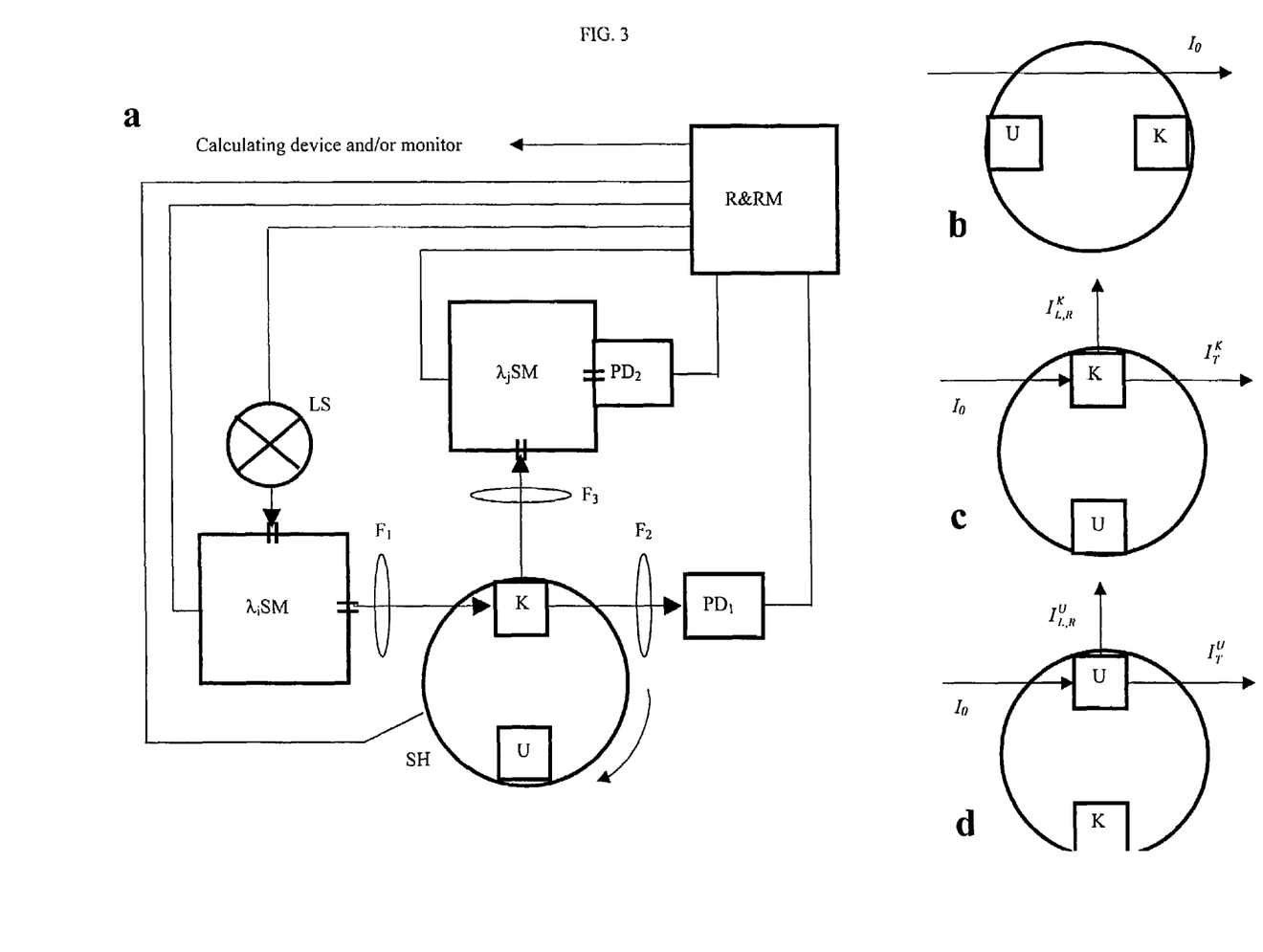
FIG. 3 is a block diagram of a specialized analytical device (a) and diagram of switching positions of samples when measuring the intensity values of the probing light $I_0$ (b), the passed light $I_T$, and the luminescent light $I_L$ (or the Raman scattering $I_R$) for a standard sample of a known mixture K (c) and a sample under analysis of an unknown compound U (d)

Step a of Example 1 is performed by a $\lambda_j$SM-module in the aggregate with a light source LS and a light-collecting device $F_1$;

- a samples holder SH performs alternate irradiation of samples (Example 1, step b) and measurements of intensity values for the probing light $I_0$, the passed light $I_T$, and the luminescent light $I_L$ of a standard sample K and an analyzed sample U (Example 1, step d), which are performed with different positions of the holder in regard to the analyzing light beam (FIG. 3 b-d);
- collecting the light falling on a sample and passed through it is performed by a light-collecting device $F_2$ to a photodetector $PD_1$, at the same time the luminescent light is disintegrated into spectral components and the required spectral section is selected from this light by a $\lambda_j$SM-module, collecting the spectral section is performed by a light-collecting device $F_3$ to a photodetector $PD_2$ (Example 1, step c);
- determining the relative intensities of the passed light and the luminescent light (Example 1, step e), which represent experimentally measured intensity values for the passed light $I_T$ and the luminescent light $I_L$ normalized for $I_0$. This is performed while processing signals are measured at different positions of the sample holder SH (FIG. 3 b-d), by the devices included in a control and registration module (R&RM), and/or further mathematical treatment implemented by an external computing device;
- the comparison of corresponding relative intensities (Example 1, step f) is performed similarly to ascertain the identity or difference of samples under analysis;
- the R&RM module also contains devices to control measurements ensuring switching of sample positions, setting the specified intervals of the selected wavelengths, and measuring signals with a specified time constant, as well as power units of light sources and photodetector (PMT) ensuring stabilization and automatic correction of power supply modes, and an interface of communication with an external computing device and/or devices of accumulation, storage and display of information.

The algorithm of comparison of characteristics of a known sample and an unknown sample provided in the present invention gives an unambiguous characteristic for the mixture under analysis, whether it corresponds with a standard sample or not. Inconsistency between a characteristic of sample under analysis and a characteristic of standard sample is evidence of a difference in their component compounds. The compliance level for a mixture under analysis and a standard sample may be characterized by the value of correlation of their absorption-luminescent signatures $\Theta$. In the simplest case, this correlation is expressed by the ratio of a number of coincident elements of matrixes $n_{i,j}$, in accordance with the analytical expressions of the methods by claims 1-4, and the total number of significant elements of matrixes N:

$$\Theta = n_{i,j}/N;$$

This is illustrated with the following nonlimiting examples:

Example 6

As an example of liquids identification, the following liquids are chosen (Table 1):

- two samples of drinking water from different sources;
- two samples of food spirit from different manufacturers;
- two samples of vodka from different manufacturers;
- two samples of motor gasoline of different types;
- two samples of shampoo of the same type from different manufacturers.

Each of the above-listed objects, by turns, is considered as a standard sample and compared by turns with the whole aggregate of tested samples for the compliance level in accordance with the method of Examples 1 and 2. As one can see in Table 1, compliance is not observed for a standard sample and tested ones for all comparisons, with the exception of total identity of samples. At the same time, objects having the same microcompound elements (water, ethanol, vodka) have the higher compliance level.

TABLE 1

| Liquid type | N° | Control sample Compliance level | | | | | | | | | |
|---|---|---|---|---|---|---|---|---|---|---|---|
| | | 1 | 2 | 3 | 4 | 5 | 6 | 7 | 8 | 9 | 10 |
| Water 1 | 1 | 1 | 0.59 | 0.7 | 0.67 | 0.67 | 0.56 | 0.35 | 0.3 | 0.2 | 0.15 |
| Water 2 | 2 | 0.59 | 1 | 0.68 | 0.66 | 0.63 | 0.52 | 0.42 | 0.37 | 0.25 | 0.28 |
| spirit 1 | 3 | 0.7 | 0.68 | 1 | 0.9 | 0.77 | 0.64 | 0.15 | 0.1 | 0.11 | 0.15 |
| spirit 2 | 4 | 0.67 | 0.66 | 0.9 | 1 | 0.76 | 0.61 | 0.12 | 0.1 | 0.15 | 0.12 |
| Vodka 1 | 5 | 0.67 | 0.63 | 0.77 | 0.76 | 1 | 0.6 | 0.25 | 0.2 | 0.23 | 0.18 |
| Vodka 2 | 6 | 0.56 | 0.52 | 0.64 | 0.61 | 0.6 | 1 | 0.23 | 0.18 | 0.25 | 0.28 |

TABLE 1-continued

| Liquid type | Control sample N° | Compliance level | | | | | | | | | |
|---|---|---|---|---|---|---|---|---|---|---|---|
| | | 1 | 2 | 3 | 4 | 5 | 6 | 7 | 8 | 9 | 10 |
| gasoline 1 | 7 | 0.35 | 0.42 | 0.15 | 0.12 | 0.25 | 0.23 | 1 | 0.68 | 0.42 | 0.37 |
| gasoline 2 | 8 | 0.3 | 0.37 | 0.1 | 0.1 | 0.2 | 0.18 | 0.68 | 1 | 0.35 | 0.32 |
| Shampoo 1 | 9 | 0.2 | 0.25 | 0.11 | 0.15 | 0.23 | 0.25 | 0.42 | 0.35 | 1 | 0.4 |
| Shampoo 2 | 10 | 0.15 | 0.28 | 0.15 | 0.12 | 0.18 | 0.28 | 0.37 | 0.32 | 0.4 | 1 |

It should be noted that ascertaining the identity of samples by comparing their differences, within the framework of the present invention, presents different tasks which differ in the amount of time required. To ascertain unambiguously the identity of objects being compared, it is necessary to determine the compliance by the greatest possible number of parameters, whereas, for ascertaining their difference, it is enough when at least one of the parameters under comparison for a mixture under analysis differs from a corresponding parameter for a standard sample. This is illustrated by Examples 7 and 8.

Example 7

In Table 2, a comparison of compliance levels is presented for pure liquids which were obtained from correlating absorption-luminescent signatures (ALS) in accordance with the method shown in Examples 1 and 2, and the same signatures supplemented by the Raman co-factor (RALS) in accordance with the processes of Examples 3 and 4. As can be seen in Table 2, adding the Raman component does not substantially change the value of the conformity level for objects related by being in the same chemical class, and results in drastic differences for objects which are in different chemical classes.

TABLE 2

| Identity method | Control sample | water | | spirit | | Cyclohexane |
|---|---|---|---|---|---|---|
| | | 1 | 2 | 3 | 4 | 5 |
| ALS | 1 | 1 | 0.59 | 0.7 | 0.67 | 0.25 |
| | 2 | 0.59 | 1 | 0.68 | 0.66 | 0.2 |
| | 3 | 0.7 | 0.68 | 1 | 0.9 | 0.4 |
| | 4 | 0.67 | 0.66 | 0.9 | 1 | 0.35 |
| | 5 | 0.25 | 0.2 | 0.4 | 0.35 | 1 |
| RALS | 1 | 1 | 0.59 | 0.18 | 0.17 | 0 |
| | 2 | 0.59 | 1 | 0.17 | 0.16 | 0 |
| | 3 | 0.18 | 0.17 | 1 | 0.85 | 0.3 |
| | 4 | 0.17 | 0.16 | 0.85 | 1 | 0.26 |
| | 5 | 0 | 0 | 0.3 | 0.26 | 1 |

Example 8

Figure 4:
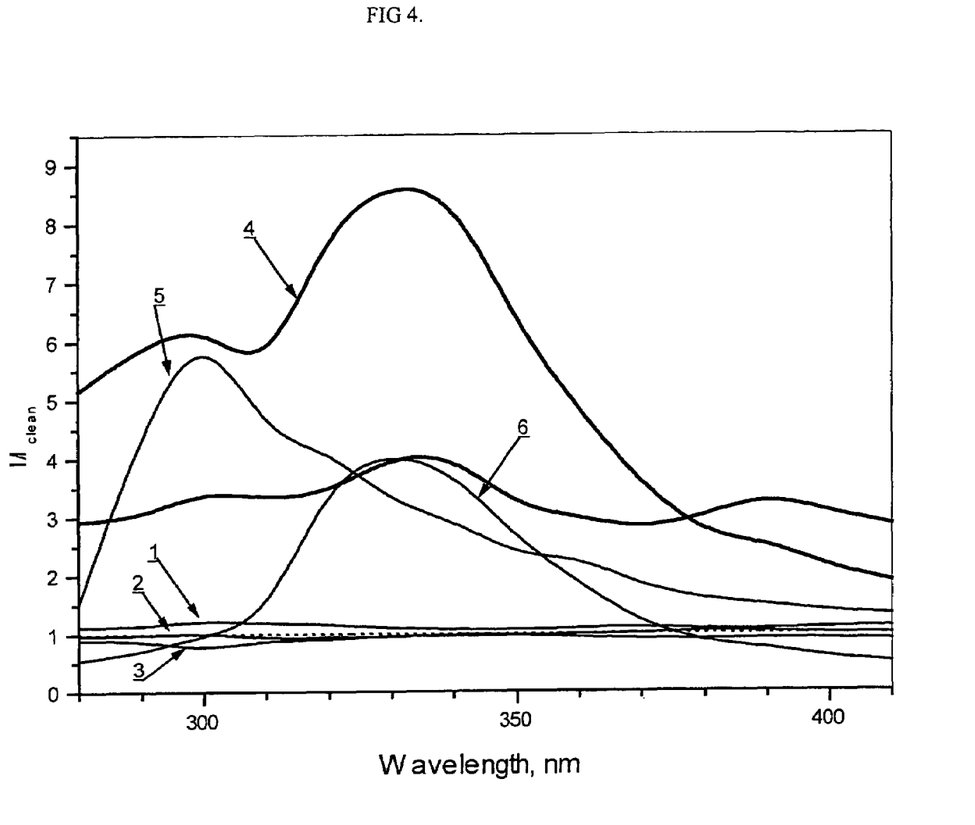
FIG. 4 shows spectra of intensity ratios for impurity luminescence of water samples with the same fixed excitation wavelength ($\lambda_{ex}=230$ nm)

In FIG. 4, correlation spectra are shown for intensity values of impurity luminescence using the same fixed excitation wavelength (230 nm) for water taken from various points of the municipal water supply system (curves 1-3 on FIG. 4) and for the same water contaminated with municipal wastewater (curve 4); 3,4-benzopyrene (curve 5); and petroleum derivatives (curve 6). As one can see from FIG. 4, all three samples of clean water have minimal differences, while at the same time the presented samples have perceptible differences using the complete set of parameters (this value for samples 1, 2, and 3, respectively, are 0.86, 0.9 and 0.95). It is clear that contaminants in the water change the situation drastically, so that users can determine that these are distinct from a standard sample only on the basis of the date presented, which reduces the analysis time by a factor of about 10-20.

Example 9

This example shows identification of a variety of industrial products produced for domestic purposes:

Three samples of dry yeast, two of which belong to the same production lot of the same manufacturer (samples 1-1 and 1-2), and a sample of a similar product from another manufacturer (sample 2);

Three samples of washing powder of the same brand from the same production lot from a well-known manufacturer (samples 1-1 and 1-2), and a sample of a similar product of another brand from the same manufacturer (sample 2);

Three samples of domestic gel-like washing liquid of the same brand, from the same production lot, from a well-known manufacturer (samples 1-1 and 1-2), and a sample of a similar product from the same manufacturer, but another brand (sample 2);

One can distinctly see in Table 3 that samples of products manufactured from strictly identical raw materials during the same processing cycle have a high compliance level with each other. This compliance is not observed when the manufacturing conditions are changed.

TABLE 3

| | | dry yeast | | | washing powder | | | domestic gel-like washing-up liquid | | |
|---|---|---|---|---|---|---|---|---|---|---|
| | N° | 1-1 | 1-2 | 2 | 1-1 | 1-2 | 2 | 1-1 | 1-2 | 2 |
| dry yeast | 1-1 | 1 | 0.95 | 0.5 | — | — | — | — | — | — |
| | 1-2 | 0.95 | 1 | 0.65 | — | — | — | — | — | — |
| | 2 | 0.5 | 0.65 | 1 | — | — | — | — | — | — |

TABLE 3-continued

|  | N° | dry yeast 1-1 | dry yeast 1-2 | dry yeast 2 | washing powder 1-1 | washing powder 1-2 | washing powder 2 | domestic gel-like washing-up liquid 1-1 | domestic gel-like washing-up liquid 1-2 | domestic gel-like washing-up liquid 2 |
|---|---|---|---|---|---|---|---|---|---|---|
| washing powder | 1-1 | — | — | — | 1 | 0.86 | 0.3 | — | — | — |
|  | 1-2 | — | — | — | 0.86 | 1 | 0.4 | — | — | — |
|  | 2 | — | — | — | 0.3 | 0.4 | 1 | — | — | — |
| domestic gel-like washing-up liquid | 1-1 | — | — | — | — | — | — | 1 | 0.9 | 0.45 |
|  | 1-2 | — | — | — | — | — | — | 0.9 | 1 | 0.4 |
|  | 2 | — | — | — | — | — | — | 0.45 | 0.4 | 1 |

Example 10

This example illustrates determining the impurities contaminating liquids, in this case, drinking water, with additives of different classes of substances. As a standard sample, clean drinking water was accepted here. The following liquids were tested for the presence of contaminants:

The standard water

The standard water with priority PAH (3,4-benzopyrene) dissolved therein; The standard water with crude petroleum dissolved therein;

The same water with organophosphorus insecticides disk solved therein Thiophos (structure 1) and foksim (structure 2);

The standard water with chlorine dissolved therein.

The standard water with medical products dissolved therein: methyl ether of benozylecognine (structure 3); 1,3, 7-trimethylxanthine (structure 4); penicillin (structure 5); and tetracycline (structure 6);

The same water containing *E. coli;*

The same water contaminated with municipal wastewater.

This example demonstrates the adaptability of the method of the present invention in monitoring water systems for the purpose of exposing contamination with either chemical or biological contaminants.

As can readily be seen from Table 4, the compliance level of water contaminated with 3,4-benzopyrene with eth standard water was reduced to one half, which compliance was reduced even more when the water was contaminated with petroleum. A similar situation was also observed in the case of contamination with substances such as organophosphorus insecticides, chlorine, medical products, bacteria, and municipal wastewater.

It should be noted that adding the chlorine resulted in a drastic reduction of the conformity level of the ALS signature of a sample being tested with a sample of clean water. At the same time, visual checks of outline maps of these objects (see FIG. 2) do not permit the user to draw the same conclusions. These facts point out the high level of accuracy of the present invention.

TABLE 4

| Contaminant | Compliance level | | |
|---|---|---|---|
| PAH | Is absent | 3,4-benzopyrene | Petroleum |
|  | 0.5 ± 0.05 | 0.48 | 0.39 |
| Organophosphorus compound | Is absent | Structure 1 | Structure 2 |
|  | 0.95 ± 0.05 | 0.43 | 0.41 |
| Chlorine | Is absent | 0.41 | |
|  | 0.95 ± 0.05 | | |

TABLE 4-continued

| Contaminant | Compliance level | | |
|---|---|---|---|
| Medical products | Is absent | Structure 3 | Structure 4 |
|  | 0.95 ± 0.05 | 0.32 | 0.46 |
|  | Is absent | Structure 5 | Structure 6 |
|  | 0.95 ± 0.05 | 0.4 | 0.36 |
| Bacteria culture | Is absent | e-coli | |
|  | 0.95 ± 0.05 | 0.5 | |
| Municipal wastewater | Is absent | 0.55 | |
|  | 0.95 ± 0.05 | | |

The foregoing description of the specific embodiments will so fully reveal the general nature of the invention that others can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to determine and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

REFERENCES

1. Lavrik, N. L. *Chemistry and Life* (magazine), XXI century, No. 3, 2000, as well as http://www.informauka.ru/rus/2000/2000-03-06-0124_r.htm.
2. Karagodin, G. M. Book on vodka and wine-making, Cheljabinsk, Ural Ltd., 1998, p. 468.
3. Dedkov, Ju. M. *Russian Chemical Magazine,* 2002, v. 46, No. 4, pp. 11-17.
4. Korte, F. Ecological chemistry. Foundation and concepts. M.; Mir, 1996, p. 396.
5. Fortoutan-Red, M. *Umwelt.,* 1982, Bd. 2, No. 2, S. 126-134.
6. Devjatykh, G. G., Kovaljov, I. D., Maksimov, G. A. *Russian Chemical Magazine,* v. 38, No. 1, p. 96 (1994).

7. Beyermann, K., Organic Trace Analysis. Georg Thieme Verlag, Stuttgart—N.Y. (1982).
8. J.-M. Lenn. Supramolecular Chemistry. VCH Verlagsgesselhaft mbH, 1995.
9. Bakhshiev, N. G. Spectroscopy of intermolecular interactions. L.: Nauka (1972).
10. Lakowicz, J. R., Principles of Fluorescence Spectroscopy, Plenum Press, New York (1983).
11. Suppan, P. *J. Photochem. and Photobiol.*, A: Chem., 1990, V. 50, P. 293-330.
12. Ingrum, J. G., et al. U.S. Pat. No. 002,397, 1991.
13. Littlejohn, D. G, et al. U.S. Pat. No. 4,998,824, 1991.
14. Webor, G. *Nature,* 1961, V.190, No. 4770, p. 27.
15. Rho, J. H., Stuart, J. L. *Anal. Chem.,* 1978, v. 50, No. 4, p. 620.
16. Corfield, M. M., Hawhins, H. L., John, P., Soutar, L. *Analyst,* 1981, v. 106, p. 188.
17. Siegel, J. A., Fisher, J., Gilna, C., et al. *Forensic Sci.,* 1985, v. 30, No. 3, p. 741.
18. Nekrasov V. V, et al., pat RU 2150699, 2000, bull. No. 16.
19. Nekrasov, V. V., Gasanov, D. R., Dejneko, A. O., et al. *Theses of the 2nd scientific and practical conference, Identification of quality and safety of alcoholic products*, Pushchino, 2000, p. 65.
20. C. N. Banwell, Fundamentals of Molecular Spectroscopy, McGraw-Hill Book Company (UK) Limited (1983).
21. Parker, C. A. Photoluminescence of Solutions. Elsevier Publishing Company. Amsterdam-London-New York, 1968.
22. Rabek, J. F. Experimental Methods in Photochemistry and Photophysics. John Wiley & Sons. Chichester-New York-Brisbane-Toronto-Singapore, 1982.

What is claimed is:

1. A method for authenticating the composition of multi-component mixtures and/or detecting the presence of impurities in multicomponent mixtures comprising:
   a. dividing the light of a broadband source of optical radiation into spectral components, and/or selecting the assigned narrow band spectral sections of the probing beam with a spectral width of $\Delta_i$ from the predetermined spectral range of wavelengths $\lambda_i$ while ensuring the possibility of changing the spectral position of these sections with the assigned pitch $\Delta\lambda_i \geq \Delta_i$;
   b. focusing the selected narrowband light onto a sample under analysis;
   c. irradiating a sample of a known mixture K and a sample of an unknown mixture U by turns with the focused probing beam at the selected wavelengths $\lambda_1, \lambda_2, \ldots \lambda_m$ from the predetermined spectral range $\lambda_i$;
   d. collecting the probing light falling on the sample, passed through the sample or reflected by the sample to a photodetector and collecting spectral sections of the luminescent light to another photodetector;
   e. measuring the intensity values of the probing light and the luminescent light collected onto the photodetectors for each of the selected wavelengths $\lambda_1, \lambda_2, \ldots \lambda_m$ of the predetermined spectral range $\lambda_i$, such that, the probing light is $I_0$, the light passed through the sample or reflected by the sample is $I_T$, and the luminescent light of the sample is $I_L$, including steps of decomposition of the luminescent light into a variety of spectral sections, and/or sequential selection of the specified sections of wavelength of $\lambda_1, \lambda_2, \ldots \lambda_n$ with a width of $\Delta_j$, with the assigned pitch of $\Delta\lambda_j \geq \Delta_j$, where each section corresponds with the predetermined characteristic wavelength of the light in the predetermined spectral range $\lambda_j$, are collecting onto the corresponding photodetectors and are measuring;
   f. determining the relative intensity of the collected light passed through the sample, or reflected by a the sample, at each of selected wavelengths $\lambda_m$, and the luminescent light for each of the selected wavelengths $\lambda_m, \lambda_n$ for the known mixture and unknown mixture, in accordance with the following expressions:

$$T^K(\lambda_m) = \frac{I_T^K(\lambda_m)}{I_0^K(\lambda_m)}; \quad T^U(\lambda_m) = \frac{I_T^U(\lambda_m)}{I_0^U(\lambda_m)};$$

$$L^K(\lambda_m, \lambda_n) = \frac{I_L^K(\lambda_m, \lambda_n)}{I_0^K(\lambda_m)}; \quad L^U(\lambda_m, \lambda_n) = \frac{I_L^U(\lambda_m, \lambda_n)}{I_0^U(\lambda_m)},$$

where
   $T^K(\lambda_m), T^U(\lambda_m)$—intensity values of passed or reflected light for samples of a known K mixture and unknown U mixture, normalized for the intensity of incident radiation falling on a sample at the corresponding wavelength;
   $L^K(\lambda_m,\lambda_n), L^U(\lambda_m,\lambda_n)$—intensity values of the luminescent light irradiated by a sample of a known K mixture and unknown U mixture within the specified sections $\lambda_1, \lambda_2, \ldots \lambda_n$ of the predetermined range of wavelengths $\lambda_j$ with light excitation within the specified sections $\lambda_1, \lambda_2, \ldots \lambda_m$ of the predetermined range of wavelengths $\lambda_i$, normalized for intensity of incident radiation falling on a sample at the corresponding wavelength;
   $I_T^K(\lambda_m), I_T^U(\lambda_m)$—intensities of passed or reflected light for samples of a known K mixture and an unknown U mixture measured at the specified sections $\lambda_1, \lambda_2, \ldots \lambda_m$ of the selected range of the incident light from the predetermined range $\lambda_i$;
   $I_L^K(\lambda_m,\lambda_n), I_L^U(\lambda_m,\lambda_n)$—intensities of the luminescence radiated by a sample of a known K mixture and a sample of an unknown U mixture measured at the selected wavelength $\lambda_1, \lambda_2, \ldots \lambda_n$ of the selected range of wavelengths $\lambda_j$ with light excitation within the specified sections $\lambda_1, \lambda_2, \ldots \lambda_m$ of the predetermined range of wavelengths $\lambda_i$;
   $I_0^K(\lambda_m), I_0^U(\lambda_m)$—intensity of incident probing radiation falling on an appropriate samples at the time of performing measurements;
   g. comparing the corresponding relative intensity values of the light passed through the sample, or reflected by the sample, at each of the selected wavelengths $\lambda_m$, and the luminescent light for each of the selected wavelengths $\lambda_m, \lambda_n$ for the known mixture and the unknown mixture, and determining the compliance between the unknown mixture and the known mixture by the following expression:

$$A = \frac{1}{2} \times \left( \frac{1}{m} \times \sum_{m=1}^{m} \frac{T^U(\lambda_m)}{T^K(\lambda_m)} + \frac{1}{m \times n} \times \sum_{m=1}^{m} \sum_{n=1}^{n} \frac{L^U(\lambda_m, \lambda_n)}{L^K(\lambda_m, \lambda_n)} \right) = 1 \pm \delta,$$

where
   m, n—the number of selected wavelengths from the predetermined spectral ranges $\lambda_i$ and $\lambda_j$, respectively;
   δ—a value of allowable deflections of the compared values for the unknown mixture under analysis from the corresponding values for the similar values of a standard sample of a known mixture;
   h. determining the presence or absence of foreign impurities in the mixture by the following expressions:

$$C_T(\lambda_i) = \frac{T^U(\lambda_{m+1})}{T^K(\lambda_{m+1})} - \frac{T^U(\lambda_m)}{T^K(\lambda_m)};$$

$$C_L(\lambda_i, \lambda_j) = \frac{L^U(\lambda_{m+1}, \lambda_{n+1})}{L^K(\lambda_{m+1}, \lambda_{n+1})} - \frac{L^U(\lambda_m, \lambda_n)}{L^K(\lambda_m, \lambda_n)};$$

whereas, if $C_T(\lambda_i)=C_L(\lambda_i,\lambda_j)=0\pm\delta$, there are no foreign impurities in the sample under analysis, while if there are ranges with $C_T(\lambda_i)>0\pm\delta$, and/or $C_L(\lambda_i,\lambda_j)\neq 0\pm\delta$, undesirable impurities are present in the sample.

2. The method according to claim 1 comprising:
 a. obtaining an electronic absorption-luminescent signature of the multicomponent mixture;
 b. comparing the electronic absorption-luminescent signatures of the sample with the electronic absorption-luminescent signature of the known mixture;
 c. preparing calibration samples which represent a specially made-up mixture or multicomponent solution of such compound, for which the absorption or reflectance spectra, and luminescence spectra of which solution (mixture) overlap with the corresponding spectra of known mixture within the predetermined analytical spectral ranges $\lambda_i$ and $\lambda_j$, i.e. have nonzero intensity in the specified ranges;
 d. placing the standard sample of the known K mixture and the calibration Q sample into an analytical device;
 e. Measuring and transforming measured values for intensity of the light passed through or reflected by the standard and calibration samples, and their luminescent light, in accordance with steps a-f of claim 1, while taking into account the step of replacing the unknown U sample with the calibration Q sample;
 f. creating an electronic absorption-luminescent signature $ALS_K$ of the standard sample as follows:

$$ALS_K = \|K_E\| = \left\| \begin{pmatrix} \left(\frac{T_1^K}{T_1^Q}\right) & \left(\frac{L_{1,1}^K}{L_{1,1}^Q}\right) & \cdots & \left(\frac{L_{1,n}^K}{L_{1,n}^Q}\right) \\ \cdots & \cdots & \cdots & \cdots \\ \left(\frac{T_m^K}{T_m^Q}\right) & \left(\frac{L_{m,1}^K}{L_{m,1}^Q}\right) & \cdots & \left(\frac{L_{m,n}^K}{L_{m,n}^Q}\right) \end{pmatrix} \right\|,$$

where:
$T_m^K$—intensities of the passed or reflected light $I_T$ of a sample of a known K mixture, normalized for intensities of the probing light $I_O$, measured at the frequencies $\lambda_m$;
$L_{m,n}^K, L_{m,n}^Q$—intensities of the luminescence radiated by a sample of a known K mixture and a calibration Q sample, normalized for intensities of the probing light $I_O$, measured at the frequencies $\lambda_n$ with the excitation at the frequencies $\lambda_m$;
 g. entering the electronic signature of the standard sample $ALS_K$ into a computer database, and/or saving the electronic signature of the standard sample on an intermediate medium;
 h. repeating step (e) with the sample of the unknown mixture, including the step of replacing the standard sample K with the calibration sample Q, which is strictly identical with the calibration sample used when measuring the standard sample, and creating an electronic signature $ALS_U$ of a sample under analysis:

$$ALS_U = \|U_E\| = \left\| \begin{pmatrix} \left(\frac{T_1^U}{T_1^Q}\right) & \left(\frac{L_{1,1}^U}{L_{1,1}^Q}\right) & \cdots & \left(\frac{L_{1,n}^U}{L_{1,n}^Q}\right) \\ \cdots & \cdots & \cdots & \cdots \\ \left(\frac{T_m^U}{T_m^Q}\right) & \left(\frac{L_{m,1}^U}{L_{m,1}^Q}\right) & \cdots & \left(\frac{L_{m,n}^U}{L_{m,n}^Q}\right) \end{pmatrix} \right\|,$$

where
$T_m^U$—intensities of the passed or reflected light $I_T$ of a sample of an unknown U mixture, normalized for intensities of the probing light $I_O$, measured at the frequencies $\lambda_m$;
$L_{m,n}^U$—intensities of the luminescence radiated by a sample of an unknown U mixture, normalized for intensities of the probing light $I_O$, measured at the frequencies $\lambda_n$ with the excitation at the frequencies $\lambda_m$;
 i. comparing the electronic signatures of the unknown mixture $ALS_U=\|U_E\|$ being tested with similar data for the standard sample of the a known mixture $ALS_K=\|K_E\|$ by the following expression:

$$\|A_{ALS}\| = \frac{\|U_E\|}{\|K_E\|},$$

such that, a conclusion on the identity of the unknown mixture and the certain mixture may be drawn when all elements of the matrix $\|A_{ALS}\|$ contain only unit elements (i.e. $a_i=a_{i,j}=1\pm\delta$;
 j. determining the presence or absence of unwanted contaminations for the mixture under study by the following expression:

$$\|C_{ALS}\| = \frac{\|U_E\| - \|K_E\|}{\|K_E\|},$$

wherein, if the matrix $\|C_{ALS}\|$ comprises nonzero elements, the values of which exceed the value of allowable deflections from the corresponding values of the standard sample of the known mixture, $|c_i, c_{i,j}|>|\pm\delta|$, the sample under analysis is determined to contain the unwanted contaminations.

3. The method according to claim 2 distinguished by comparing electronic signatures containing, along with spectral profiles of absorption and luminescent intensities, spectral profiles of Raman scattering intensities for the unknown ($RALS_U$) and the standard sample ($RALS_K$), wherein the Raman matrixes are normalized in the following way:
 a. preparing a calibration sample $Q_R$, which calibration sample represents a specially made-up mixture or a multicomponent solution of such compound, for which the absorption or reflectance, and luminescence spectrum of which overlaps with the Raman spectrum of the known mixture within the predetermined analytical spectral ranges;
 b. measuring the intensity of Raman scattering, converting the results as in steps d-h of claim 1, and forming the electronic Raman signatures of the standard sample and the unknown mixture being identified in accordance with the following expressions:

$$\|K_R\| = \left\| \begin{pmatrix} \left(\frac{R_{1,1}^K}{L_{1,1}^{Q_R}}\right) & \cdots & \left(\frac{R_{1,p}^K}{L_{1,p}^{Q_R}}\right) \\ \cdots & \cdots & \cdots \\ \left(\frac{R_{q,1}^K}{L_{q,1}^{Q_R}}\right) & \cdots & \left(\frac{R_{q,p}^K}{L_{q,p}^{Q_R}}\right) \end{pmatrix} \right\| \text{ и } \|U_R\| = \left\| \begin{pmatrix} \left(\frac{R_{1,1}^U}{L_{1,1}^{Q_R}}\right) & \cdots & \left(\frac{R_{1,p}^U}{L_{1,p}^{Q_R}}\right) \\ \cdots & \cdots & \cdots \\ \left(\frac{R_{q,1}^U}{L_{q,1}^{Q_R}}\right) & \cdots & \left(\frac{R_{q,p}^U}{L_{q,p}^{Q_R}}\right) \end{pmatrix} \right\|,$$

where $R_{q,p}^K, R_{q,p}^U$—intensity values of Raman scattering light, normalized for intensity of the exciting light $I_{ex}$, for samples of a known K mixture and an unknown U mixture, measured at the frequencies $v_p$ with light excitation at the frequency $v_q$;

$L_{q,p}^{Q_R}$—the luminescence intensity for a calibration sample $Q_R$, normalized for the intensity of the exciting light $I_{ex}$;

c. comparing the electronic signatures of the unknown mixture $\|U_E\|$ being tested with similar data for the standard sample of the known mixture $\|K_E\|$, including the step of comparing electronic Raman matrixes (RALS$_{U,K}$), by the following expression:

$$\|A_{RALS}\| = \left(\frac{\|U_R\|}{\|K_R\|}\right) \times \left(\frac{\|U_E\|}{\|K_E\|}\right),$$

where the identity of samples is determined by the following attribute: $\|A_{RALS}\| = 1 \pm \delta$.

4. The method according to claim 1 further comprising measuring intensity values of Raman scattering of the sample under analysis and the standard sample including the following steps:

a. irradiating the samples the unknown and the known mixture, by turns, with a monochromatic line of a narrow-band (lined) source of light at one or several selected fixed frequencies $v_r$;

b. collecting the light of Raman scattering onto the photodetector device;

c. measuring the intensity of the light on each of the selected frequencies $v_1, v_2, \ldots, v_p$ of the predetermined spectral range, collected onto the photodetector, namely: the exciting light falling on the sample $I_{ex}$, and the light of Raman scattering of the sample $I_R$, including steps of decomposition of the light of Raman scattering into a variety of spectral sections, and/or sequential selection of the specified frequency sections $v_1, v_2, \ldots, v_p$ with a width of $\Delta_r$, with assigned pitch $\Delta v_r \geqq \Delta_r$, where each section corresponds to the predetermined characteristic frequency of the light in the predetermined spectral range $v_r$, are collected onto the corresponding photodetectors and are measured;

d. determining the relative intensity of the collected light of Raman scattering at each of the selected frequencies $v_1, v_2, \ldots v_p$ for the known and unknown mixtures in accordance with the following expressions:

$$R^K(v_{ex}, v_p) = \frac{I_R^K(v_{ex}, v_p)}{I_{ex}^K}; \quad R^U(v_{ex}, v_p) = \frac{I_R^U(v_{ex}, v_p)}{I_{ex}^U};$$

where:

$I_R^K(v_{ex}, v_p), I_R^U(v_{ex}, v_p)$—intensity values of Raman scattering radiated by a sample of a known K mixture and a sample of an unknown U mixture within the specified sections $v_1, v_2, \ldots v_p$ of the predetermined frequency range $v_r$ with light excitation at one of the selected frequencies $v_{ex}$;

$I_{ex}^K, I_{ex}^U$—intensity values of the exciting light falling on corresponding samples at the time of performing measurements; e. comparing data for the mixture being tested with similar data for the standard sample of the known mixture by the following expression:

$$A = \frac{1}{2} \times \left(\frac{R^U(v_{ex}, v_p)}{R^K(v_{ex}, v_p)}\right) \times \left(\frac{1}{m} \times \sum_{m=1}^{m} \frac{T^U(\lambda_m)}{T^K(\lambda_m)} + \frac{1}{m \times n} \times \sum_{m=1}^{m} \sum_{n=1}^{n} \frac{L^U(\lambda_m, \lambda_n)}{L^K(\lambda_m, \lambda_n)}\right),$$

wherein the unknown mixture and the known mixture are determined as being identical if $A = 1 \pm \delta$.

5. The method according to claim 1 wherein the sample of the mixture under analysis and the standard mixture are dissolved in appropriate solvents.

6. The method of claim 1 wherein the method comprises detection of multicomponent impurities in aqueous systems.

\* \* \* \* \*